(12) United States Patent
Zusman

(10) Patent No.: US 9,528,903 B2
(45) Date of Patent: Dec. 27, 2016

(54) PIEZOELECTRIC VIBRATION SENSOR FOR FLUID LEAK DETECTION

(71) Applicant: Mueller International, LLC, Atlanta, GA (US)

(72) Inventor: George V. Zusman, Houston, TX (US)

(73) Assignee: Mueller International, LLC, Atlanta, GA (US)

( * ) Notice: Subject to any disclaimer, the term of this patent is extended or adjusted under 35 U.S.C. 154(b) by 195 days.

(21) Appl. No.: 14/503,951

(22) Filed: Oct. 1, 2014

(65) Prior Publication Data

US 2016/0097696 A1   Apr. 7, 2016

(51) Int. Cl.

| | |
|---|---|
| *G01M 3/24* | (2006.01) |
| *G01H 11/08* | (2006.01) |
| *F17D 5/06* | (2006.01) |
| *H04R 17/00* | (2006.01) |
| *H01L 41/08* | (2006.01) |
| *E03B 7/00* | (2006.01) |
| *G01L 1/18* | (2006.01) |
| *G01N 29/04* | (2006.01) |
| *F16L 55/28* | (2006.01) |
| *G01M 3/00* | (2006.01) |
| *F16L 101/30* | (2006.01) |

(52) U.S. Cl.
CPC ............... *G01M 3/24* (2013.01); *E03B 7/003* (2013.01); *F16L 55/28* (2013.01); *F17D 5/06* (2013.01); *G01H 11/08* (2013.01); *G01L 1/183* (2013.01); *G01M 3/005* (2013.01); *G01M 3/243* (2013.01); *G01M 3/246* (2013.01); *G01N 29/04* (2013.01); *H04R 17/00* (2013.01); *F16L 2101/30* (2013.01)

(58) Field of Classification Search
CPC ......... G01M 3/24; G01M 3/243; H04R 17/00; G01H 11/08; F17D 5/06; E03B 7/00; E03B 7/003; G01N 29/04; H01L 41/00; H01L 41/02; H01L 41/08; H01L 41/18

See application file for complete search history.

(56) References Cited

U.S. PATENT DOCUMENTS

| | | |
|---|---|---|
| 2,286,437 A | 6/1942 | Odell |
| 3,592,967 A | 7/1971 | Harris |
| 3,612,922 A | 10/1971 | Furnival |

(Continued)

FOREIGN PATENT DOCUMENTS

| | | |
|---|---|---|
| CA | 2397174 | 8/2008 |
| CA | 2725065 | 11/2009 |

(Continued)

OTHER PUBLICATIONS

Fleury, Jr., Leo W.; Notice of Allowance for U.S. Appl. No. 13/492,790, filed Jun. 8, 2012, mailed May 12, 2015, 9 pgs.

(Continued)

*Primary Examiner* — Nguyen Ha

(74) *Attorney, Agent, or Firm* — Taylor English Duma LLP

(57) ABSTRACT

A vibration sensor includes at least one piezoelectric crystal having an upper surface and a lower surface; a base having an attachment section defining an attachment surface and an at least one calibration mass; wherein a one of the at least one piezoelectric crystal upper surface and lower surface attaches to the attachment surface of the base; and wherein the at least one calibration mass is external to the piezoelectric crystal.

20 Claims, 7 Drawing Sheets

(56) References Cited

U.S. PATENT DOCUMENTS

| | | |
|---|---|---|
| 3,673,856 A | 7/1972 | Panigati |
| 3,815,129 A | 6/1974 | Sweany |
| 4,056,970 A | 11/1977 | Sollish |
| 4,083,229 A | 4/1978 | Anway |
| 4,156,156 A * | 5/1979 | Sweany .............. G10K 9/122 29/25.35 |
| 4,333,028 A | 6/1982 | Panton |
| 4,431,873 A | 2/1984 | Dunn et al. |
| 4,462,249 A | 7/1984 | Adams |
| 4,467,236 A * | 8/1984 | Kolm ................ H01L 41/1138 310/321 |
| 4,543,817 A | 10/1985 | Sugiyama |
| 4,727,279 A | 2/1988 | Peng |
| 4,930,358 A | 6/1990 | Motegi et al. |
| 4,984,498 A | 1/1991 | Fishman |
| 5,038,614 A | 8/1991 | Bseisu et al. |
| 5,052,215 A | 10/1991 | Lewis |
| 5,078,006 A | 1/1992 | Maresca et al. |
| 5,085,082 A | 2/1992 | Cantor et al. |
| 5,090,234 A | 2/1992 | Maresca et al. |
| 5,117,676 A | 6/1992 | Chang |
| 5,118,464 A | 6/1992 | Richardson et al. |
| 5,163,314 A | 11/1992 | Maresca et al. |
| 5,165,280 A | 11/1992 | Sternberg et al. |
| 5,170,657 A | 12/1992 | Maresca et al. |
| 5,174,155 A | 12/1992 | Sugimoto |
| 5,187,973 A | 2/1993 | Kunze et al. |
| 5,189,904 A | 3/1993 | Maresca et al. |
| 5,201,226 A | 4/1993 | John et al. |
| 5,203,202 A | 4/1993 | Spencer |
| 5,205,173 A | 4/1993 | Allen |
| 5,209,125 A | 5/1993 | Kalinoski et al. |
| 5,218,859 A | 6/1993 | Stenstrom et al. |
| 5,243,862 A | 9/1993 | Latimer |
| 5,254,944 A | 10/1993 | Holmes et al. |
| 5,272,646 A | 12/1993 | Farmer |
| 5,279,160 A | 1/1994 | Koch |
| 5,287,884 A | 2/1994 | Cohen |
| 5,303,592 A | 4/1994 | Livingston |
| 5,319,956 A | 6/1994 | Bogle et al. |
| 5,333,501 A | 8/1994 | Okada et al. |
| 5,335,547 A | 8/1994 | Nakajima et al. |
| 5,343,737 A | 9/1994 | Baumoel |
| 5,349,568 A | 9/1994 | Kupperman et al. |
| 5,351,655 A | 10/1994 | Nuspl |
| 5,361,636 A | 11/1994 | Farstad et al. |
| 5,367,911 A | 11/1994 | Jewell et al. |
| 5,385,049 A | 1/1995 | Hunt et al. |
| 5,396,800 A | 3/1995 | Drinon et al. |
| 5,408,883 A | 4/1995 | Clark et al. |
| 5,416,724 A | 5/1995 | Savic |
| 5,461,906 A | 10/1995 | Bogle et al. |
| 5,519,184 A | 5/1996 | Umlas |
| 5,526,691 A | 6/1996 | Latimer et al. |
| 5,531,099 A | 7/1996 | Russo |
| 5,548,530 A | 8/1996 | Baumoel |
| 5,581,037 A | 12/1996 | Kwun et al. |
| 5,591,912 A | 1/1997 | Spisak et al. |
| 5,602,327 A | 2/1997 | Torizuka et al. |
| 5,611,948 A | 3/1997 | Hawkins |
| 5,619,423 A | 4/1997 | Scrantz |
| 5,623,203 A | 4/1997 | Hosohara et al. |
| 5,633,467 A | 5/1997 | Paulson |
| 5,639,958 A | 6/1997 | Lange |
| 5,655,561 A | 8/1997 | Wendel et al. |
| 5,686,828 A | 11/1997 | Peterman et al. |
| 5,708,195 A | 1/1998 | Kurisu et al. |
| 5,708,211 A | 1/1998 | Jepson et al. |
| 5,760,306 A | 6/1998 | Wyatt et al. |
| 5,789,720 A | 8/1998 | LaGally et al. |
| 5,798,457 A | 8/1998 | Paulson |
| 5,838,633 A | 11/1998 | Sinha |
| 5,866,820 A | 2/1999 | Camplin et al. |
| 5,892,163 A | 4/1999 | Johnson |
| 5,907,100 A | 5/1999 | Cook |
| 5,965,818 A | 10/1999 | Wang |
| 5,970,434 A | 10/1999 | Brophy et al. |
| 5,974,862 A | 11/1999 | Lander et al. |
| 5,987,990 A | 11/1999 | Worthington et al. |
| 6,000,277 A | 12/1999 | Smith |
| 6,000,288 A | 12/1999 | Kwun et al. |
| 6,003,376 A | 12/1999 | Burns et al. |
| 6,023,986 A | 2/2000 | Smith et al. |
| 6,035,717 A | 3/2000 | Carodiskey |
| 6,076,407 A | 6/2000 | Levesque et al. |
| 6,082,193 A | 7/2000 | Paulson |
| 6,125,703 A | 10/2000 | MacLauchlan et al. |
| 6,127,823 A | 10/2000 | Atherton |
| 6,138,512 A | 10/2000 | Roberts et al. |
| 6,138,514 A | 10/2000 | Iwamoto et al. |
| 6,164,137 A | 12/2000 | Hancock et al. |
| 6,170,334 B1 | 1/2001 | Paulson |
| 6,175,380 B1 | 1/2001 | Van Den Bosch |
| 6,192,352 B1 | 2/2001 | Alouani et al. |
| 6,243,657 B1 | 6/2001 | Tuck et al. |
| 6,267,000 B1 | 7/2001 | Harper et al. |
| 6,276,213 B1 | 8/2001 | Lee et al. |
| 6,296,066 B1 | 10/2001 | Terry |
| 6,363,788 B1 | 4/2002 | Gorman et al. |
| 6,389,881 B1 | 5/2002 | Yang et al. |
| 6,401,525 B1 | 6/2002 | Jamieson |
| 6,404,343 B1 | 6/2002 | Andou et al. |
| 6,442,999 B1 | 9/2002 | Baumoel |
| 6,453,247 B1 | 9/2002 | Hunaidi |
| 6,470,749 B1 | 10/2002 | Han et al. |
| 6,530,263 B1 | 3/2003 | Chana |
| 6,561,032 B1 | 5/2003 | Hunaidi |
| 6,567,006 B1 | 5/2003 | Lander et al. |
| 6,578,422 B2 | 6/2003 | Lam et al. |
| 6,595,038 B2 | 7/2003 | Williams et al. |
| 6,624,628 B1 | 9/2003 | Kwun et al. |
| 6,647,762 B1 | 11/2003 | Roy |
| 6,651,503 B2 | 11/2003 | Bazarov et al. |
| 6,666,095 B2 | 12/2003 | Thomas et al. |
| 6,667,709 B1 | 12/2003 | Hansen et al. |
| 6,707,762 B1 | 3/2004 | Goodman et al. |
| 6,710,600 B1 | 3/2004 | Kopecki et al. |
| 6,725,705 B1 | 4/2004 | Huebler et al. |
| 6,745,136 B2 | 6/2004 | Lam et al. |
| 6,751,560 B1 | 6/2004 | Tingley et al. |
| 6,772,636 B2 | 8/2004 | Lam et al. |
| 6,772,637 B2 | 8/2004 | Bazarov et al. |
| 6,772,638 B2 | 8/2004 | Matney et al. |
| 6,781,369 B2 | 8/2004 | Paulson et al. |
| 6,782,751 B2 | 8/2004 | Linares et al. |
| 6,789,427 B2 | 9/2004 | Batzinger et al. |
| 6,791,318 B2 | 9/2004 | Paulson et al. |
| 6,799,466 B2 | 10/2004 | Chinn |
| 6,813,949 B2 | 11/2004 | Masaniello et al. |
| 6,813,950 B2 | 11/2004 | Glascock et al. |
| 6,816,072 B2 | 11/2004 | Zoratti |
| 6,820,016 B2 | 11/2004 | Brown et al. |
| 6,822,742 B1 | 11/2004 | Kalayeh et al. |
| 6,843,131 B2 | 1/2005 | Graff et al. |
| 6,848,313 B2 | 2/2005 | Krieg et al. |
| 6,851,319 B2 | 2/2005 | Ziola et al. |
| 6,889,703 B2 | 5/2005 | Bond |
| 6,904,818 B2 | 6/2005 | Harthorn et al. |
| 6,920,792 B2 | 7/2005 | Flora et al. |
| 6,931,931 B2 | 8/2005 | Graff et al. |
| 6,935,178 B2 | 8/2005 | Prause |
| 6,945,113 B2 | 9/2005 | Siverling et al. |
| 6,957,157 B2 | 10/2005 | Lander |
| 6,968,727 B2 | 11/2005 | Kwun et al. |
| 6,978,832 B2 | 12/2005 | Gardner et al. |
| 7,051,577 B2 | 5/2006 | Komninos |
| 7,080,557 B2 | 7/2006 | Adnan |
| 7,111,516 B2 | 9/2006 | Bazarov et al. |
| 7,140,253 B2 | 11/2006 | Merki et al. |
| 7,143,659 B2 | 12/2006 | Stout et al. |
| 7,171,854 B2 | 2/2007 | Nagashima et al. |
| 7,231,331 B2 | 6/2007 | Davis |
| 7,234,355 B2 | 6/2007 | Dewangan et al. |
| 7,240,574 B2 | 7/2007 | Sapelnikov |

(56) References Cited

U.S. PATENT DOCUMENTS

| | | | |
|---|---|---|---|
| 7,255,007 B2 | 8/2007 | Messer et al. | |
| 7,261,002 B1 | 8/2007 | Gysling et al. | |
| 7,266,992 B2 | 9/2007 | Shamout et al. | |
| 7,284,433 B2 | 10/2007 | Ales et al. | |
| 7,293,461 B1 | 11/2007 | Girndt | |
| 7,299,697 B2 | 11/2007 | Siddu et al. | |
| 7,310,877 B2 | 12/2007 | Cao et al. | |
| 7,328,618 B2 | 2/2008 | Hunaidi et al. | |
| 7,331,215 B2 | 2/2008 | Bond | |
| 7,356,444 B2 | 4/2008 | Blemel | |
| 7,360,462 B2 | 4/2008 | Nozaki et al. | |
| 7,373,808 B2 | 5/2008 | Zanker et al. | |
| 7,380,466 B2 | 6/2008 | Deeg | |
| 7,383,721 B2 | 6/2008 | Parsons et al. | |
| 7,392,709 B2 | 7/2008 | Eckert | |
| 7,405,391 B2 | 7/2008 | Ogisu et al. | |
| 7,412,890 B1 | 8/2008 | Johnson et al. | |
| 7,414,395 B2 | 8/2008 | Gao et al. | |
| 7,418,354 B1 | 8/2008 | Greenlee et al. | |
| 7,426,879 B2 | 9/2008 | Nozaki et al. | |
| 7,458,267 B2 | 12/2008 | McCoy | |
| 7,475,596 B2 | 1/2009 | Hunaidi et al. | |
| 7,493,817 B2 | 2/2009 | Germata | |
| 7,523,666 B2 | 4/2009 | Thompson et al. | |
| 7,526,944 B2 | 5/2009 | Sabata et al. | |
| 7,530,270 B2 | 5/2009 | Nozaki et al. | |
| 7,543,500 B2 | 6/2009 | Litzenberg et al. | |
| 7,554,345 B2 | 6/2009 | Vokey | |
| 7,564,540 B2 | 7/2009 | Paulson | |
| 7,587,942 B2 | 9/2009 | Smith et al. | |
| 7,590,496 B2 | 9/2009 | Blemel | |
| 7,596,458 B2 | 9/2009 | Lander | |
| 7,607,351 B2 | 10/2009 | Allison et al. | |
| 7,623,427 B2 | 11/2009 | Jann et al. | |
| 7,647,829 B2 | 1/2010 | Junker et al. | |
| 7,650,790 B2 | 1/2010 | Wright | |
| 7,657,403 B2 | 2/2010 | Stripf et al. | |
| 7,668,670 B2 | 2/2010 | Lander | |
| 7,680,625 B2 | 3/2010 | Trowbridge et al. | |
| 7,690,258 B2 | 4/2010 | Minagi et al. | |
| 7,694,564 B2 | 4/2010 | Brignac et al. | |
| 7,711,217 B2 | 5/2010 | Takahashi et al. | |
| 7,751,989 B2 | 7/2010 | Owens et al. | |
| 7,810,378 B2 | 10/2010 | Hunaidi et al. | |
| 7,980,317 B1 | 7/2011 | Preta et al. | |
| 8,018,126 B2* | 9/2011 | Umeki | H03H 9/0595 |
| | | | 310/344 |
| 8,319,508 B2 | 11/2012 | Vokey | |
| 8,415,860 B2* | 4/2013 | Malkin | H02N 2/186 |
| | | | 310/309 |
| 8,620,602 B2 | 12/2013 | Alonso | |
| 8,674,830 B2 | 3/2014 | Lanham et al. | |
| 8,843,241 B2 | 9/2014 | Saberi et al. | |
| 9,048,419 B2* | 6/2015 | Xu | G01P 15/09 |
| 9,291,520 B2 | 3/2016 | Fleury, Jr. et al. | |
| 2001/0045129 A1 | 11/2001 | Williams et al. | |
| 2002/0043549 A1 | 4/2002 | Taylor et al. | |
| 2002/0159584 A1 | 10/2002 | Sindalovsky et al. | |
| 2003/0107485 A1 | 6/2003 | Zoratti | |
| 2003/0167847 A1 | 9/2003 | Brown et al. | |
| 2004/0264416 A1 | 12/2004 | Robinson et al. | |
| 2005/0005680 A1 | 1/2005 | Anderson | |
| 2005/0279169 A1 | 12/2005 | Lander | |
| 2006/0283251 A1 | 12/2006 | Hunaidi | |
| 2007/0051187 A1 | 3/2007 | McDearmon | |
| 2007/0113618 A1 | 5/2007 | Yokoi et al. | |
| 2007/0130317 A1 | 6/2007 | Lander | |
| 2008/0078567 A1 | 4/2008 | Miller et al. | |
| 2008/0300803 A1 | 12/2008 | Drake et al. | |
| 2008/0307623 A1 | 12/2008 | Furukawa | |
| 2009/0058088 A1 | 3/2009 | Pitchford et al. | |
| 2009/0182099 A1 | 7/2009 | Noro et al. | |
| 2009/0214941 A1 | 8/2009 | Buck et al. | |
| 2009/0216353 A1 | 8/2009 | Van Reck | |
| 2009/0278293 A1 | 11/2009 | Yoshinaka et al. | |
| 2010/0089127 A1 | 4/2010 | Farnsworth | |
| 2010/0156632 A1 | 6/2010 | Hyland et al. | |
| 2010/0236036 A1* | 9/2010 | Stark | B60C 23/041 |
| | | | 29/25.35 |
| 2010/0290201 A1 | 11/2010 | Takeuchi et al. | |
| 2010/0295672 A1 | 11/2010 | Hyland et al. | |
| 2010/0312502 A1 | 12/2010 | Alonso | |
| 2011/0066297 A1 | 3/2011 | Saberi | |
| 2011/0308638 A1 | 12/2011 | Hyland et al. | |
| 2012/0007743 A1 | 1/2012 | Solomon | |
| 2012/0007744 A1 | 1/2012 | Pal et al. | |
| 2012/0079872 A1 | 4/2012 | Schaefer et al. | |
| 2012/0272722 A1 | 11/2012 | Khalifa et al. | |
| 2013/0036796 A1 | 2/2013 | Fleury, Jr. et al. | |
| 2013/0257224 A1 | 10/2013 | Wodnicki | |
| 2015/0247777 A1* | 9/2015 | Kondou | F17D 5/06 |
| | | | 73/49.1 |
| 2016/0097674 A1 | 4/2016 | Zusman | |

FOREIGN PATENT DOCUMENTS

| | | | |
|---|---|---|---|
| CA | 2634739 | 6/2015 | |
| DE | 4211038 | 10/1993 | |
| EP | 1052492 | 11/2000 | |
| EP | 1077370 | 2/2001 | |
| EP | 1077371 | 2/2001 | |
| FR | 2439990 | 5/1980 | |
| FR | 2776065 | 9/1999 | |
| GB | 2250820 | 6/1992 | |
| GB | 2269900 | 2/1994 | |
| GB | 2367362 | 4/2002 | |
| GB | 2421311 | 6/2006 | |
| JP | 59170739 | 9/1984 | |
| JP | 60111132 | 6/1985 | |
| JP | 63195573 | 8/1988 | |
| JP | 08250777 | 9/1996 | |
| JP | 2002206965 | 7/2002 | |
| JP | 2007300426 A * | 11/2007 | H04R 17/00 |
| WO | 9850771 | 11/1998 | |
| WO | 0151904 | 7/2001 | |
| WO | 2007069150 | 6/2007 | |
| WO | 2009067770 | 6/2009 | |
| WO | 2009143287 | 11/2009 | |
| WO | 2011021039 | 2/2011 | |
| WO | 2011058561 | 5/2011 | |
| WO | 2012000088 | 1/2012 | |
| WO | 2012153147 | 11/2012 | |
| WO | 2013025526 | 2/2013 | |
| WO | 2014066764 | 5/2014 | |

OTHER PUBLICATIONS

Fleury, Jr., Leo W.; Final Office Action for U.S. Appl. No. 13/492,795, filed Jun. 8, 2012, mailed May 22, 2015, 28 pgs.

Fleury Jr., Leo W.; European Search Report for serial No. 12823594, filed Aug. 10, 2012, mailed Jun. 8, 2015, 11 pgs.

Non-Patent Literature "Radiodetection Water Leak Detection Products", 2008, Radiodetection Ltd.—SPX Corporation.

Fleury, Jr., Leo W.; Issue Notification for U.S. Appl. No. 13/492,790, filed Jun. 8, 2012, mailed Mar. 2, 2016, 1 pg.

Fleury, Jr., Leo W.; Notice of Allowance for U.S. Appl. No. 13/492,790, filed Jun. 8, 2012, mailed Feb. 2, 2016, 9 pgs.

Leury, Jr., Leo W.; Non-Final Office Action for U.S. Appl. No. 13/492,795, filed Jun. 8, 2012, mailed Mar. 1, 2016, 42 pgs.

Bracken, Marc; Written Opinion for Singapore application No. 11201503041s, filed Oct. 25, 2013, mailed Jan. 5, 2016, 7 pgs.

Fleury, Jr., Leo W.; Notice of Allowance for U.S. Appl. No. 13/492,790, filed Jun. 8, 2012, mailed Sep. 23, 2015, 11 pgs.

Fleury, Leo W.; U.S. Continuation Application entitled: Leak Detector having U.S. Appl. No. 14/870,070, filed Sep. 30, 2015, 80 pgs.

Fleury, Jr., Leo W.; Advisory Action for U.S. Appl. No. 13/492,790, filed Jun. 8, 2012, mailed Jul. 9, 2014, 3 pgs.

Fleury, Jr., Leo W.; Final Office Action for U.S. Appl. No. 13/492,790, filed Jun. 8, 2012, mailed Mar. 12, 2014; 19 pgs.

Fleury, Jr., Leo W.; Non-Final Office Action for U.S. Appl. No. 13/492,790, filed Jun. 8, 2012, mailed Sep. 12, 2013; 37 pgs.

(56) References Cited

OTHER PUBLICATIONS

Fleury, Jr., Leo W.; U.S. Patent Application Entitled: Fire Hydrant Leak Detector under U.S. Appl. No. 13/492,790, filed Jun. 8, 2012, 69 pgs.
Fleury, Jr., Leo W.; U.S. Patent Application Entitled: Leak Detector and Sensor under U.S. Appl. No. 13/492,792, filed Jun. 8, 2012, 68 pgs.
Richarz, Werner Guenther; Non-Final Office Action for U.S. Appl. No. 13/492,792, filed Jun. 8, 2012, mailed Nov. 6, 2013, 39 pgs.
Richarz, Werner Guenther; Non-Final Office Action for U.S. Appl. No. 13/492,792, filed Jun. 8, 2012, mailed Jun. 4, 2014, 24 pgs.
Richarz, Werner Guenther; Restriction Requirement for U.S. Appl. No. 13/492,792, filed Jun. 8, 2012, mailed Sep. 27, 2013; 5 pgs.
Fleury, Jr., Leo W.; U.S. Patent Application Entitled: Leak Detector under U.S. Appl. No. 13/492,794, filed Jun. 8, 2012, 69 pgs.
Fleury Jr, Leo W.; Non-Final Office Action for U.S. Appl. No. 13/492,795, filed Jun. 8, 2012, mailed Sep. 23, 2013; 35 pgs.
Fleury, Jr., Leo W.; Advisory Action for U.S. Appl. No. 13/492,795, filed Jun. 8, 2012, mailed Jun. 18, 2014, 4 pgs.
Fleury, Jr., Leo W.; Final Office Action for U.S. Appl. No. 13/492,795, filed Jun. 8, 2012, mailed Apr. 23, 2014, 19 pgs.
Fleury, Jr., Leo W.; U.S. Patent Application Entitled: Enclosure for Leak Detector under U.S. Appl. No. 13/492,795, filed Jun. 8, 2012, 68 pgs.
Fleury, Leo W.; International Preliminary Report on Patentability for serial No. PCT/US12/50390 filed Aug. 10, 2012, mailed Feb. 18, 2014, 14 pgs.
Fleury, Leo W.; International Search Report and Written Opinion for serial No. PCT/US12/50390 filed Aug. 10, 2012, mailed Dec. 17, 2012, 18 pgs.
Jr., Leo W.; PCT Application Entitled: Fire Hydrant Leak Detector under serial No. PCT/US12/50390, filed Aug. 10, 2012, 80 pgs.
Fleury, Leo W., U.S. Provisional Patent Application Entitled: Hydrant Leak Detector Communication Device, System, and Method under U.S. Appl. No. 61/523,274, filed Aug. 12, 2011; 35 pgs.
Fleury Jr, Leo W.; Non-Final Office Action for U.S. Appl. No. 13/492,790, filed Jun. 8, 2012, mailed Nov. 5, 2014, 30 pgs.
Richarz, Werner Guenther; Final Office Action for U.S. Appl. No. 13/492,792, filed Jun. 8, 2012, mailed Oct. 20, 2014, 17 pgs.
Fleury, Jr., Leo W.; Non-Final Office Action for U.S. Appl. No. 13/492,795, filed Jun. 8, 2012, mailed Oct. 21, 2014, 37 pgs.
Richarz, Werner Guenther; Non-Final Office Action for U.S. Appl. No. 13/492,792, filed Jun. 8, 2012, mailed Feb. 27, 2015, 15 pgs.
Dintakurti, Ganapathi Deva Varma; Non-Final Office Action for U.S. Appl. No. 13/492,794, filed Jun. 8, 2012, mailed Jan. 16, 2015, 60 pgs.
Fleury, et al.; Supplemental European Search Report for application No. 12823594.2, filed Aug. 20, 2012, mailed Feb. 18, 2015, 6 pgs.
J.A. Gallego-Juarez, G. Rodriguez-Corral and L. Gaete-Garreton, An ultrasonic transducer for high power applications in gases, Nov. 1978, Ultrasonics, published by IPC Business Press, p. 267-271.
Richarz, Werner Guenther; Final Office Action for U.S. Appl. No. 13/492,792, filed Jun. 8, 2012, mailed Sep. 10, 2015, 20 pgs.

Fleury, Jr., Leo W.; Advisory Action for U.S. Appl. No. 13/492,795, filed Jun. 8, 2012, mailed Sep. 9, 2015, 3 pgs.
Bracken, Marc; U.S. Patent Application entitled: Detecting Leaks in a Fluid Distribution System, having U.S. Appl. No. 14/063,334, filed Oct. 25, 2013, 34 pgs.
Hunaidi, Osama; Issue Notification for U.S. Appl. No. 11/766,288, filed Jun. 21, 2007, mailed Sep. 22, 2010, 1 pg.
Hunaidi, Osama; Non-Final Office Action for U.S. Appl. No. 11/766,288, filed Jun. 21, 2007, mailed Jan. 20, 2010, 50 pgs.
Hunaidi, Osama; Notice of Allowance for U.S. Appl. No. 11/766,288, filed Jun. 21, 2007, mailed Jun. 24, 2010, 8 pgs.
Hunaidi, Osama; U.S. Patent Application entitled: Monitoring of Leakage in Wastewater Force Mains and Other Pipes Carrying Fluid under Pressure, having U.S. Appl. No. 11/766,288, filed Jun. 21, 2007, 33 pgs.
Bracken, Mark; International Preliminary Report on Patentability for serial No. PCT/US2013/066817, filed Oct. 25, 2013, mailed Apr. 28, 2015, 8 pgs.
Bracken, Mark; International Search Report and Written Opinion for serial No. PCT/US2013/066817, filed Oct. 25, 2013, mailed Mar. 18, 2014, 9 pgs.
Bracken, Mark; PCT Application entitled: Detecting Leaks in a Fluid Distribution System, having serial No. PCT/US13/66817, filed Oct. 25, 2013, 33 pgs.
Bracken, Marc; U.S. Provisional Application entitled: Detecting Leaks in Water Pipes, having U.S. Appl. No. 61/719,320, filed Oct. 26, 2012, 33 pgs.
Richarz, Werner Guenther; Non-Final Office Action for U.S. Appl. No. 13/492,792, filed Jun. 8, 2012, mailed Mar. 8, 2016, 27 pgs.
Bracken, Marc; Partial Supplementary European Search Report for European application No. 13849336.6, filed Oct. 15, 2013, mailed Mar. 11, 2016, 7 pgs.
Zusman, George V.; Extended European Search Report for serial No. 15188004.4, filed Oct. 1, 2015, mailed Feb. 22, 2016, 9 pgs.
Non-Patent Literature (Bimorph) (entitled "Bimoprh actuators"), accessed at http://web.archive.org/web/20080122050424/http://www.elpapiezo.ru/eng/curve_e.shtml, archived on Jan. 22, 2008.
Non-Patent Literature Murata (entitled "Piezoelectric Sounds Components"), accessed at http://web.archive.org/web/20030806141815/http://www.murata.com/catalog/p37e17.pdf, archived on Aug. 6, 2003.
Non-Patent Literature NerdKits, accessed at http://web.archive.org/web/20090510051850/http://www.nerdkits.com/videos/sound_meter/, archived on May 10, 2009.
Machine translation for JPH0711534, mailed on Sep. 2, 2016, 5 pgs.
Chou, et al.; Article entitled: "Non-invasive Acceleration-based Methodology for Damage Detection and Assessment of Water Distribution System", Mar. 2010, 17 pgs.
Dintakurti, Ganapathi Deva Varma; Non-Final Office Action for U.S. Appl. No. 13/492,794, filed Jun. 8, 2012, mailed May 17, 2016, 48 pgs.
Bracken, Marc; Non-Final Office Action for U.S, U.S. Appl. No. 14/063,334, filed Oct. 25, 2013, mailed Jul. 26, 2016, 87 pgs.
Bracken, Marc; European Search Report for European application No. 13849336.6, filed Oct. 15, 2013, mailed Jul. 11, 2016, 13 pgs.

* cited by examiner

PIEZOELECTRIC VIBRATION SENSOR FOR FLUID LEAK DETECTION

TECHNICAL FIELD

This disclosure relates to vibration sensors. More specifically, this disclosure relates to piezoelectric vibration sensors for fluid leak detection.

BACKGROUND

Water utility companies provide water to customers through a network of water pipes. The size of pipes may vary depending on the volume of water that is designed to flow through a particular section of pipe. For example, large water mains may provide water transportation to a location farther away from the source of the water and the size of pipes may decrease as the volume and distance from the source decreases. One concern for water utility companies, as well as the owners and operators of other fluid distribution and transportation systems, is the loss of fluid through leaks in the pipes. Not only do fluid leaks waste fluids, such as clean potable water, but sometimes unwanted contaminants may be introduced into the fluid system from outside the system through the point of the leak.

Piezoelectric vibration sensors are a type of vibration sensor that typically include a piezoelectric crystal capable of generating a current when the crystal is bent during vibrations. The piezoelectric crystal is typically attached to a base of the vibration sensor and another piezoelectric crystal may be attached to the base such that the base is between the two piezoelectric crystals. The vibration sensor may also include more than two piezoelectric crystals or more than one base. The current from the one or more piezoelectric crystals during vibration can then be detected to sense vibrations. Fluid systems such as water distribution systems may vibrate when a leak is present in the system, and a vibration sensor can detect these vibrations to signal when the system should be shut down, inspected, or treated to repair the leak. Leaks in fluid systems in various conditions and situations may produce different vibrations in different frequency ranges, requiring vibration sensors attached to the systems to be calibrated to respond appropriately during a desired frequency range that would indicate a leak for a particular system in a particular situation. In some situations, leaks in a fluid system fall within a frequency range typically lower than the frequency detection range of typical piezoelectric vibration sensors. Therefore the vibration sensor requires a specific resonance frequency that is specifically tailored to fall within the frequency range of typical leaks of the specific fluid system to which the vibration sensor is attached to. The reverse also holds true in some situations where it is desired that the resonance is outside the measured frequency range if there is a possibility of amplifying ambient noise or distorting the frequency profile.

SUMMARY

Disclosed is a sensor including at least one piezoelectric crystal having an upper surface and a lower surface; a base having an attachment section defining an attachment surface and an at least one calibration mass; wherein a one of the at least one piezoelectric crystal upper surface and lower surface attaches to the attachment surface of the base; and wherein the at least one calibration mass is external to the piezoelectric crystal.

Also disclosed is a method of manufacturing a sensor including forming a base of the vibration sensor with an attachment section defining an attachment surface and at least one calibration mass, the at least one calibration mass external to the attachment section, the calibration mass having a calibration mass thickness greater than a thickness of the attachment section of the base; and attaching a piezoelectric crystal to the attachment surface of the attachment section of the base.

Also disclosed is a method of detecting vibrations with a sensor including attaching the sensor to a piping member, the sensor including at least one piezoelectric crystal having an upper surface and a lower surface; and a base having an attachment section and at least one calibration mass; wherein the attachment section defines an attachment surface; wherein a one of the upper surface and the lower surface of the at least one piezoelectric crystal attaches to the attachment surface of the base; and the at least one calibration mass being external to the piezoelectric crystal; monitoring a signal output of the sensor; receiving a signal output from the sensor; and determining that the signal indicates that a vibration has been sensed.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Disclosed is a vibration sensor and associated methods, systems, devices, and various apparatus. In various embodiments, the vibration sensor includes a piezoelectric crystal and a base having an attachment section and calibration mass exterior to the attachment section. It would be understood by one of skill in the art that the disclosed vibration sensor is described in but a few exemplary embodiments among many. No particular terminology or description should be considered limiting on the disclosure or the scope of any claims issuing therefrom.

Minimizing leaks in a fluid system is recognized as a critical success factor, especially for water distribution utilities, especially due to the scarcity of fresh water supplies in some locales, the costs of water treatment, and the costs for water distribution. Many municipal piping systems hold pressures in excess of several hundred pounds per square inch (psi or lb./in.$^2$). When a leak forms in a piping member, the leaking water produces vibrations as it passes from inside the piping member to outside. Under the pressure of the municipal piping system, vibrations in the piping member can be of frequencies in the audible range and can be of detectable amplitude. Many vibrations range typically from 0 Hz to 3000 Hz.

The vibration sensors of the present disclosure are compatible with all distribution pipe types, including, metallic, concrete, PVC pipes and repair sleeves, as well as valves and fittings. For example, in various embodiments, the vibration sensor may be attached to a fire hydrant, water main, pipe coupling, gate valve, meter, etc. When a leak forms in a piping member, the leaking fluid typically produces vibrations as it passes from inside the piping member to outside. Using this data that is sensed by the vibration sensor in contact with the fluid pipes, valves, or fittings, leaks can be detected. The leak detection information can be communicated to the utility provider or other third party for further analysis. Depending on the type of leak, maintenance personnel may be deployed to inspect, repair, or replace leaky pipes, valves, fittings, connections, or other components in the fluid system.

Figure 1:
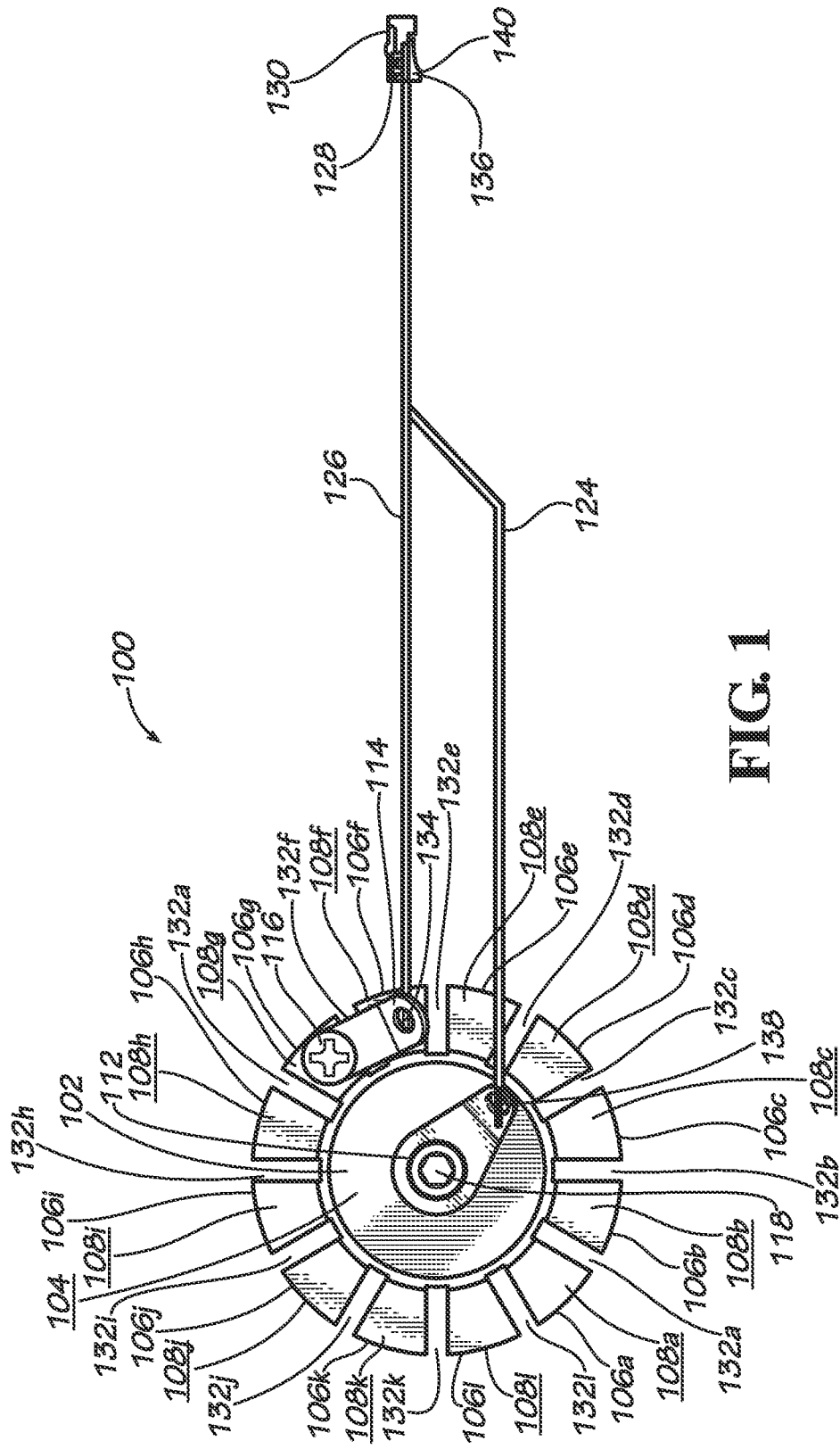
FIG. 1 is a top view of a vibration sensor in accordance with one embodiment of the current disclosure.

One embodiment of a vibration sensor 100 is shown in FIG. 1. The vibration sensor 100 includes a first piezoelectric crystal 102, a base 400 (shown in FIG. 4), and a second piezoelectric crystal 302 (shown in FIG. 3). In the current embodiment, the first piezoelectric crystal 102 and second piezoelectric crystal 302 are discs formed from piezoelectric crystals which are highly responsive to alterations and generate an electric current in response to bending. In the current embodiment, the material forming the piezoelectric crystals 102,302 thus generates a current in response to a vibration.

Figure 4:
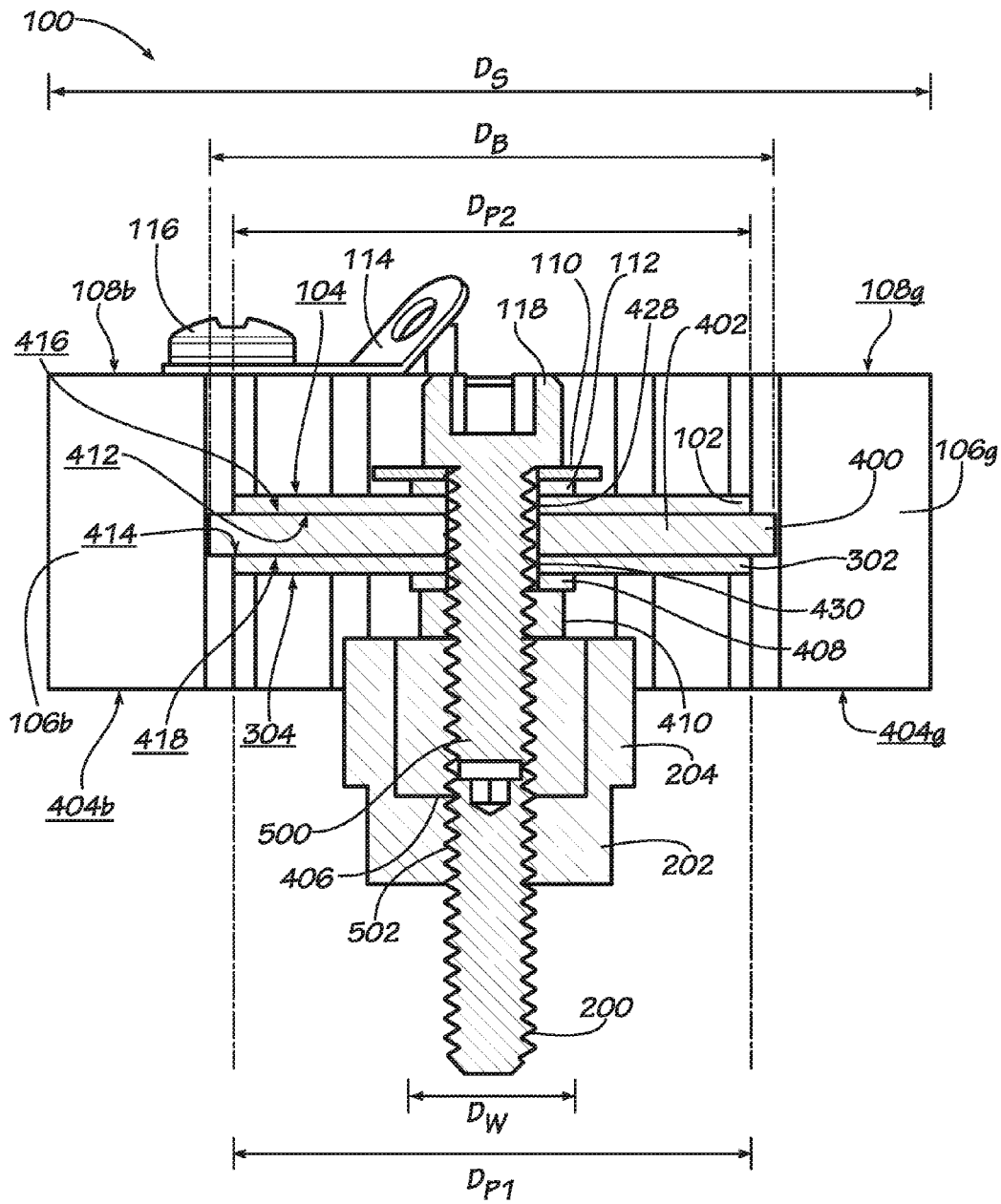
FIG. 4 is a cross-sectional view of the vibration sensor shown in FIG. 1 taken along line 4-4 in FIG. 3.

As shown in FIG. 4, in various embodiments, the base 400 may include an attachment section 402 and N calibration masses 106. Each calibration mass 106 is positioned exterior to the attachment section 402 in the current embodiment. In the current embodiment, N =12 and the base has twelve calibration masses 106a-l. Although N=12 in the current embodiment, the base 400 may have any number of calibration masses 106, including one, two, or more calibration masses 106. In various other embodiments, N may be any preferred number of calibration masses.

Additionally, in various embodiments, the calibration masses 106 may be spaced equally and radially around the base 400 exterior to the attachment section 402 such that the angles between calibration masses 106 may be 120°, 90°, 72°, 60°, 45°, or any other angle. Furthermore, in various embodiments, the calibration masses 106 may be spaced asymmetrically or at varying angles around the base 400. In addition, in various embodiments, the base 400 may define N notches 132 between calibration masses 106. In the current embodiment, N=12 and the base has twelve notches 132a-l. Although N=12 in the current embodiment, the base 400 may have any number of notches 132 including one or more notches 132. In various other embodiments, N may be any preferred number of notches 132. Each calibration mass 106 may have an upper surface 108. In the current embodiment, because the base has twelve calibration masses, twelve upper surfaces 108a-l are disclosed. In various other embodiments, the number of upper surfaces 108 is the same number N of calibration masses 106. In various embodiments, the shape, size, length, or location of the calibration masses may be used to regulate a stiffness of the sensor 100.

Additionally, in various embodiments, the base 400 may define N notches 132 between calibration masses 106. In the current embodiment, N=12 and the base has twelve notches 132a-l. Although N=12 in the present embodiment, the base 400 may have any number of notches 132 including one or more notches 132. In various other embodiments, N may be any preferred number of notches 132. In various embodiments, the notches 132 may be spaced equally around the base 400 such that the angles between notches 132 may be 120°, 90°, 72°, 60°, 45°, or any other angle. In the current embodiment, the notches 132 may be symmetrical cuts spaced equally around the perimeter of the base 400. In various embodiments, the notches 132 may be spaced asymmetrically or at varying angles around the base 400. In various embodiments, the notches 132 may be used to regulate the stiffness of the sensor 100 without significantly changing a total mass of the sensor 100. As will be discussed with reference to FIG. 9, in various embodiments, the stiffness of the sensor 100 may be adjusted by the presence of calibration masses 106 and notches 132 in the base 400 to regulate the sensitivity and resonance frequency of the vibration sensor 100 depending on the desired application.

The attachment section 402 of the base 400 includes an upper attachment surface 416 and a lower attachment surface 418 (shown in FIG. 4). In the current embodiment, the first piezoelectric crystal 102 contacts the upper attachment surface 416 and the second piezoelectric crystal 302 contacts the lower attachment surface 418. In the current embodiment, the first piezoelectric crystal 102 and the second piezoelectric crystal 302 are attached to the upper attachment surface 416 and the lower attachment surface 418, respectively, by conductive adhesive, as described below, though other attachment mechanisms may be present in various embodiments. In the current embodiment, the calibration masses 106 are positioned exterior to the first piezoelectric crystal 102 and the second piezoelectric crystal 302 radially outward from the first piezoelectric crystal 102 and the second piezoelectric crystal 302 when the first piezoelectric crystal 102 and the second piezoelectric crystal 302 are in contact with the attachment section 402 of the base 400.

As shown in FIG. 1, in various embodiments, the vibration sensor 100 may further include a first washer 112 and a second washer 408 (shown in FIG. 4). In various embodiments, the first washer 112 and second washer 408 may define a washer width $D_W$. In the current embodiment, washer width $D_W$ is 0.217", though other washer widths $D_W$ may be present in various embodiments and the disclosed dimensions should not be considered limiting on the current disclosure. In various embodiments, the vibration sensor 100 may also include a first contact 110 and a second contact 114. The first contact 110 may define a fastener hole. The second contact 114 also may define a fastener hole. Although two contacts are shown in the current embodiment, in various other embodiments, the vibration sensor may include a third contact that may define a fastener hole. In various other embodiments, one or less or more than three contacts may be present. In addition, in various embodiments the vibration sensor 100 may also include a bolt 118. In various other embodiments, another securing mechanism may be included. Additionally, in the current embodiment, the vibration sensor 100 may also include a contact screw 116 for fastening the second contact 114 onto a one of the calibration masses 106. In the current embodiment, contact screw 116 fastens second contact 114 to upper surface 108*g* of calibration mass 106*g*. In various embodiments, the bolt 118 and attachment screw 200 may fasten into a first bore 500 and a second bore 502, respectively (shown in FIG. 4). However, in other embodiments, another securing mechanism may be included. In various other embodiments, a variety of fasteners may be used and would be understood by one of skill in the art, including gluing, welding, sealing with a sealant, or providing mating threading on a pipe 612, other fixture, or spacer portion 204 of a nut 202, among other fastening mechanisms. However, in various other embodiments, a variety of fasteners may be used and would be understood by one of skill in the art, including gluing, welding, sealing with a sealant, or providing mating threading on a pipe, other fixture, or spacer, among other fastening mechanisms.

As stated elsewhere in this disclosure, the piezoelectric material may produce an electrical charge in response to bending, and a waveform of charge may be produced when the piezoelectric material is exposed to vibration. As such, in various embodiments, a charge differential between the first piezoelectric crystal 102, base 400, and second piezoelectric crystal 302 upon bending of the piezoelectric material may be used to sense the characteristics of vibrations to which the vibration sensor 100 has been exposed, such as frequency or amplitude of the vibration.

As shown in FIG. 1, in various embodiments, the vibration sensor 100 may also include a first wire 124 having a first end 138 and a second end 136. The vibration sensor 100 may also include a second wire 126 having a first end 134 and a second end 140. In various embodiments, the first end 138 of the first wire 124 may be connected to the first contact 110 by soldering and the second end 136 may be connected to a terminal 130 in a connector housing 128. Furthermore, in various embodiments, the second wire 126 first end 134 may be connected to the second contact 114 by soldering and the second end 140 may be connected to a terminal 130 in connector housing 128. In various other embodiments, the first end 138 may be connected directly to the first piezoelectric crystal 102, the base 400, the washer 112, or bolt 118. In various other embodiments, the first end 138 may be connected directly to the second piezoelectric crystal 302, the base 400, a second washer, or nut 202 (shown in FIG. 2). In various other embodiments, the first wire 124 and second wire 126 may be connected to the piezoelectric crystals 102,302, base 400, washer 112, bolt 118, nut 202 or any other desired location on the vibration sensor 100 by any preferred attachment mechanism. For example, in various embodiments, the wires 124,126 may be connected to the vibration sensor 100 at various locations with an adhesive The wires 124,126 may allow connection to a processing device or another electrical device so that the charge differential may be handled electronically, which may include recordation, amplification, summation, digital processing, and a number of other electrical features, described elsewhere in this disclosure. Although two wires are shown in the current embodiment, in various other embodiments, the vibration sensor may include a third wire with a first end and second end. In these various other embodiments, the first end of the third wire may be connected to a third contact and the second end of the third wire may be connected to a terminal in a connector housing. In these various other embodiments, the wires may also be connected to a piezoelectric crystal, base, washer, nut, or bolt.

Figure 2:
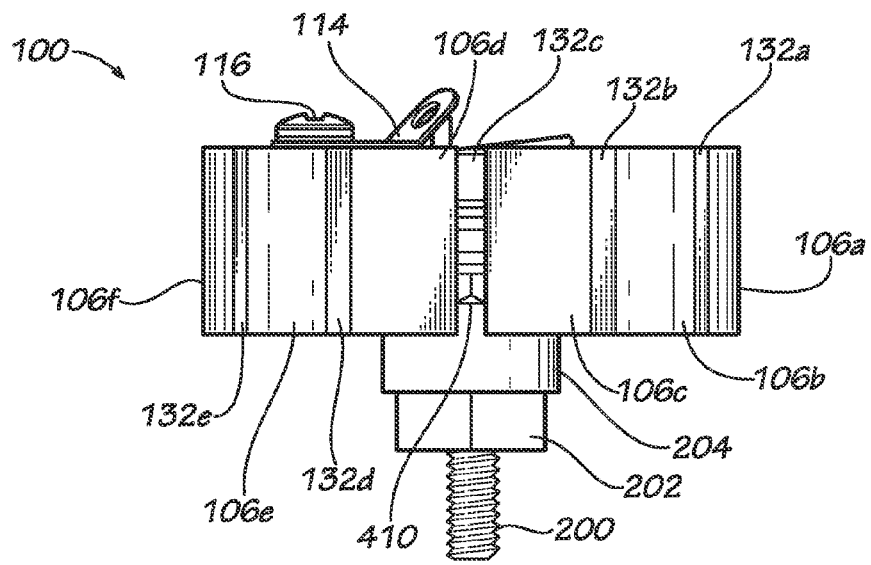
FIG. 2 is a side view of the vibration sensor shown in FIG. 1.

A side view of the vibration sensor 100 is shown in FIG. 2. As shown in FIG. 2, in various embodiments, the vibration sensor 100 may also include a nut 202 and nut 410. The nut 410 engages the bolt 118 to hold the piezoelectric crystals 102,302 and base 400 in place. In various embodiments, the nut 202 and nut 410 may be made from aluminum; however, in various other embodiments the nut 202 and nut 410 may be made from other materials. In the current embodiment, the nut 202 also includes a spacer portion 204 In various embodiments, the spacer portion 204 may have a cylindrical shape; however, in various other embodiments, the spacer portion 204 may have a different shape. In the current embodiment, the spacer portion 204 has a wider diameter than a lower portion of the nut 202.

In the current embodiment, an insulator insert 406 is inserted into an opening defined in the spacer portion 204 of the nut 202. In the current embodiment, the insulator insert 406 is press fit into the spacer portion 204, though in other embodiments the insulator insert 406 may be attached to the nut 202 by other methods, such as gluing, welding, threading, ribs and grooves, or the use of fasteners. In various embodiments, the insulator insert 406 is made of a non-conductive insulator material. For example, in various embodiments, the insulator insert 406 is made of fiberglass. In the current embodiment, the spacer 204 is made from fiberglass G-10; however, in various other embodiments, any suitable insulator material may be used to make the insulator insert 406.

The insulator insert 406 defines a first bore 500 and the nut 202 defines a second bore 502. In the current embodiment, the first bore 500 and second bore 502 may define a continuous opening through the nut 202. In the current embodiment, the first bore 500 and second bore 502 are threaded openings for mating with a bolt, screw, or other threaded securing device. As shown in FIG. 4, in various embodiments, the first bore 500 mates with the bolt 118 and the second bore 502 mates with an attachment screw 200. In various embodiments, the vibration sensor 100 may include the attachment screw 200 for fastening of the vibration sensor 100 in a fluid system.

Figure 3:
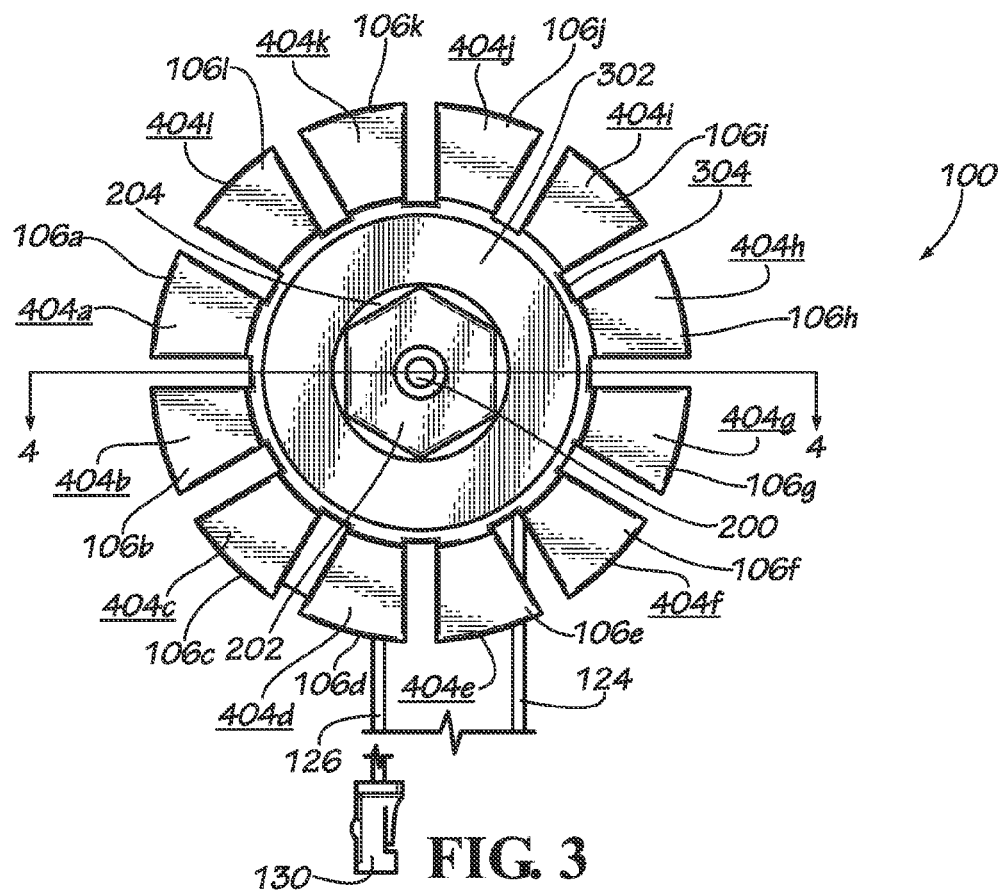
FIG. 3 is a bottom view of the vibration sensor shown in FIG. 1.

A bottom view of the vibration sensor 100 is shown in FIG. 3. As shown in FIG. 3, in various embodiments the calibration masses 106 may have a lower surface 404. In the current embodiment, because the base has twelve calibration masses, twelve lower surfaces 404*a-l* are disclosed. In various other embodiments, the number of lower surfaces 404 is equal to the number N of calibration masses 106.

A cross-sectional view of the vibration sensor 100 is shown in FIG. 4. As shown in FIG. 4, in various embodiments, the first piezoelectric crystal 102 includes an upper surface 104, a lower surface 412, and a fastener hole 428. As shown in FIG. 4, in various embodiments, the second piezoelectric crystal 302 may include a lower surface 304, an upper surface 414, and a fastener hole 430. In various embodiments, both the first piezoelectric crystal 102 and second piezoelectric crystal 302 may be a disc; however, other shapes may be used in various other embodiments. In various embodiments, the first piezoelectric crystal 102 also may define a width $D_{P1}$. The second piezoelectric crystal 302 may also define a width $D_{P2}$. In the current embodiment, widths $D_{P1}$ and $D_{P2}$ are each 0.670", though other widths $D_{P1}$ and $D_{P2}$ may be present in various embodiments and the disclosed dimensions should not be considered limiting on the current disclosure. Although in the current embodiment widths $D_{P1}$ and $D_{P2}$ are equal, in various other embodiments $D_{P1}$ may have a different value than $D_{P2}$. In various embodiments, the ratio of $D_W:D_{P1}$ or $D_W:D_{P2}$ may be 1:4. In various other embodiments, the ratio of $D_W:D_{P1}$ or $D_W:D_{P2}$ may be 1:3. At width ratios of 1:4 or 1:3 the width $D_W$ of the first washer 112 and second washer 408 may provide the vibration sensor 100 with an optimized strength with maximum sensitivity. In various other embodiments, for example for hard vibration applications, the ratio of $D_W:D_{P1}$ or $D_W:D_{P2}$ may be 1:2 or another ratio.

As shown in FIG. 4, in various embodiments, the base 400 may provide a substrate for deposition of other components of the vibration sensor 100. In various embodiments, the first piezoelectric crystal 102 and second piezoelectric crystal 302 may be bonded to the base 400. In these embodiments, a conductive adhesive may be used to bond the first piezoelectric crystal 102 and second piezoelectric crystal 302 to the base 400. More specifically, the adhesive allows for conductivity and flexibility in the current embodiment. In various embodiments, a silver conductive epoxy adhesive is the conductive adhesive. In the current embodiment, the 8330S Silver Conductive Epoxy Adhesive: Slow Cure/Extreme Conductivity epoxy sold by MG Chemicals® may be used as the conductive adhesive. In other various embodiments, the piezoelectric crystals 102,302 may be bonded or attached to the base 400 through other suitable means such as double-sided tape, various glues, various coatings including elastomeric and silicon coatings among others, pure adhesives, or by a fastener such as bolt 118. In various embodiments, the base 400 may be a disc and may be made of brass; however, various materials and shapes may be present in various other embodiments. As shown in FIG. 4, in various embodiments, the base 400 includes the attachment section 402 and N calibration masses 106 exterior to the attachment section 402. In various embodiments, the attachment section 402 of the base 400 may include the upper attachment surface 416, the lower attachment surface 418, and a fastener hole. The attachment section 402 may further define a width $D_B$. In the current embodiment, width $D_B$ is 0.375", though other widths $D_B$ may be present in various embodiments and the disclosed dimensions should not be considered limiting on the current disclosure. In various embodiments, $D_B \geq D_{P1}$ and $D_B \geq D_{P2}$.

As shown in FIG. 4, the calibration masses 106 are thick sections of the base 400 on the exterior of the attachment section 402. In various embodiments, the calibration masses 106 may further define a width $D_S$. In the current embodiment, width $D_S$ is 0.750", though other widths $D_S$ may be present in various embodiments and the disclosed dimensions should not be considered limiting on the current disclosure. In various embodiments, $D_S \geq D_B$. In various embodiments, the shape, size, or length of the calibration masses may be used to regulate the stiffness of the sensor 100. In the current embodiment, the calibration masses 106 are wedge-shaped and have a rectangular cross-section as shown in FIG. 4. However, in other various embodiments, the shape and cross-section of the calibration masses may be different, such as a triangular or circular cross-section or a cylindrical or rectangular cuboid shape. In addition, as shown in FIG. 4, in various embodiments, the upper surface 108 of the calibration masses 106 may extend above the upper surface 104 of the first piezoelectric crystals 102. Additionally, the lower surface 404 of the calibration masses 106 may extend below the lower surface 304 of the second piezoelectric crystals 302. However, in various other embodiments, the upper surface 108 may not extend above the upper surface 104 or the lower surface 404 may not extend below the lower surface 304.

In the current embodiment, the calibration masses 106 are formed integrally with the attachment section 402, with the base 400 formed from a single piece of material and thereafter machined to include notches 132 and calibration masses 106 that are thicker than attachment section 402. However, in various embodiments the calibration masses 106 may be attached to attachment section 402 using other methods, such as welding, adhesives, casting from a single mold, or fasteners, and the disclosure of machining a single piece of material to form an integral base 400 should not be considered limiting on the current disclosure.

Figure 5:
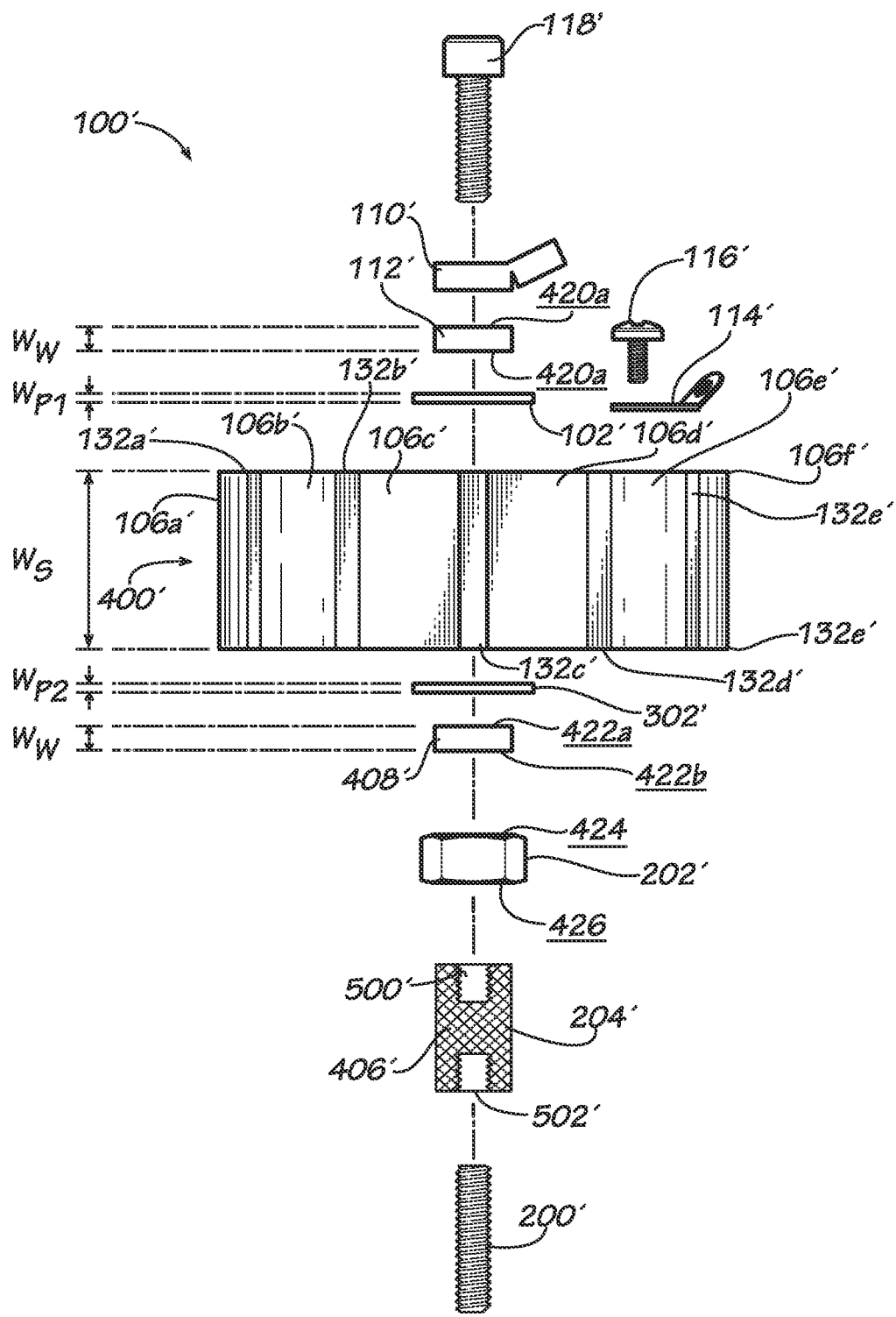
FIG. 5 is an exploded side view of a vibration sensor in accordance with another embodiment of the current disclosure with a spacer of the vibration sensor shown in cross-section.

FIG. 5 is exploded side view of a vibration sensor 100' in accordance with another embodiment of the current disclosure with a spacer 204' shown in cross-section. As shown in FIG. 5, in various embodiments, the first piezoelectric crystal 102' also may define a thickness $W_{P1}$. The second piezoelectric crystal 302' may also define a thickness $W_{P2}$. In the current embodiment, thicknesses $W_{P1}$ and $W_{P2}$ are each 0.025", though other thicknesses $W_{P1}$ and $W_{P2}$ may be present in various embodiments and the disclosed dimensions should not be considered limiting on the current disclosure. Although in the current embodiment thicknesses $W_{P1}$ and $W_{P2}$ are equal, in various other embodiments $W_{P1}$ may have a different value than $W_{P2}$.

As shown in FIG. 5, the calibration masses 106' of the base 400', which is similar to base 400 in the current embodiment, may define a thickness $W_S$. In the current embodiment, thickness $W_S$ is 0.4", though other thicknesses $W_S$ may be present in various embodiments and the disclosed dimensions should not be considered limiting on the current disclosure. In various embodiments, the calibration masses 106' all have the same thickness $W_S$; however, in various other embodiments, the thicknesses of the calibration masses 106' may be different from each other. For example, a calibration mass 106a' may have a different thickness than calibration mass 106b', or calibration masses 106a',b',c' may have a different thickness than calibration masses 106d'-l'. In the current embodiment, the thickness $W_S$ may be greater than $W_{P1}+W_{P2}$; however, in other embodiments, $W_S$ may be greater than $W_{P1}$ or $W_{P2}$.

Figure 6:
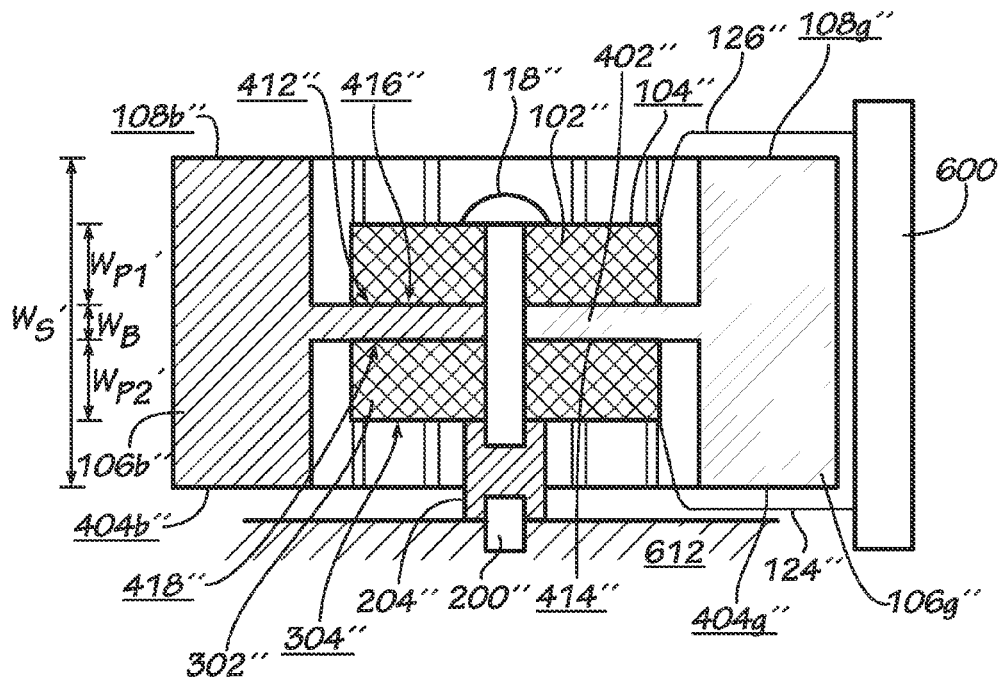
FIG. 6 is a cross-sectional view of a vibration sensor in accordance with another embodiment of the current disclosure and taken along line 6-6 in FIG. 7 when the vibration sensor is attached to a pipe.

As shown in FIG. 5, in various embodiments, the first washer 112' may have a polishing surface 420a,b. The second washer 408' may also have a polishing surface 422a,b. Furthermore, in various embodiments, a first nut 202' may have a first surface 424 and second surface 426. In the current embodiment, the nut 202' engages a bolt 118' to hold the piezoelectric crystals 102',302' and base 400' in place. Furthermore, in various embodiments, the vibration sensor 100' includes the spacer 204'. In various embodiments, the spacer 204' may have a cylindrical shape; however, in various other embodiments, the spacer 204' may have another shape. In various embodiments, the diameter of spacer 204' may be less than the diameter of the first nut 202'. In various other embodiments, the diameter of the spacer 204' may be greater than the diameter of the first nut 202'. As shown in FIG. 5, in various embodiments, the spacer 204' may define a first bore 500' and a second bore 502' separated by a middle portion 406'. In the current embodiment, the spacer 204' may be formed from an insulator material; however, in various other embodiments, the middle portion 406' may be the only insulator material of the spacer 204'. The first bore 500' may define an opening in the spacer 204' for mating with the bolt 118'. The second bore 502' may define an opening in the spacer 204' for mating with the attachment screw 200'. In various other embodiments, the first bore 500' and second bore 502' may define a continuous opening through the spacer 204'. In the current embodiment, the first bore 500 and second bore 502 are threaded openings for mating with a bolt 118'; however, in various other embodiments, the first bore 500' and second bore 502' may be threaded to mate with another bolt, screw, or other threaded securing device. As indicated by FIG. 6, in various embodiments, the first bore 500' mates with the bolt 118' and the second bore 502' mates with an attachment screw 200'. In various embodiments, the vibration sensor 100' may include the attachment screw 200' for fastening of the vibration sensor 100' in a fluid system.

Figure 7:
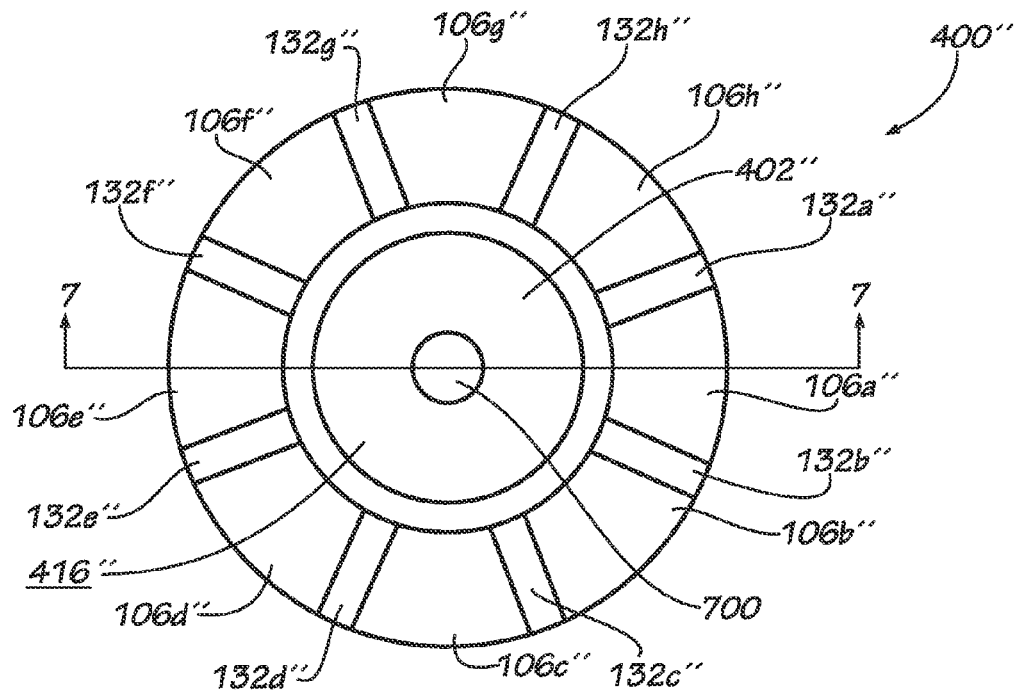
FIG. 7 is a top view of a base of a vibration sensor in accordance with another embodiment of the current disclosure.

FIG. 6 is a cross-sectional view of a vibration sensor 100" in accordance with another embodiment of the current disclosure and taken along line 6-6 in FIG. 7. As shown, in various embodiments, the vibration sensor 100" may be connected via wires 126" and 124" to a circuit board 600 where the current may processed for the detection of a leak. Additionally, in various embodiments, the vibration sensor 100" may be attached to a pipe 612 with an attachment screw 200". In various other embodiments, the vibration sensor 100" may not be in direct contact with the piping 612. In these various other embodiments, the vibration sensor 100" may be enclosed in an outer casing or housing. In various embodiments, the housing may be made of aluminum to form an aluminum casing. In various embodiments, the vibration sensor 100" may be in an aluminum casing that mounts onto a hydrant cap. In other embodiments, the housing may be made of steel to form a steel casing. In particular, in various embodiments, the vibration sensor 100" may be in a steel outer casing mounted on a pipe. In yet other various embodiments, any preferred material may be used to form the outer casing. When an outer housing is included, the outer housing may be attached to the vibration sensor and a pipe through screws, magnets, or any other suitable attachment mechanism. In various embodiments, the vibration sensor 100" may include magnets to attach to the outer housing and the outer housing may include magnets to attach to the side of a pipe. In other embodiments, straps, adhesives, screws, bolts, welding, or other fastening mechanisms may be substituted for magnets.

As shown in FIG. 6, in various embodiments, the first piezoelectric crystal 102" also may define a thickness $W_{P1}'$. The second piezoelectric crystal 302' may define a thickness $W_{P2}'$. In various embodiments, $W_{P1}'$ are $W_{P2}'$ equal; however, in various alternate embodiments, $W_{P1}'$ may have a different value than $W_{P2}'$. In addition, in various embodiments, the base 400" includes an attachment section 402" and calibration masses 106" exterior to the attachment section 402". The attachment section 402" may further define a thickness $W_B'$. In the current embodiment, thickness $W_B'$ is 0.050", though other thicknesses $W_B'$ may be present in various embodiments and the disclosed dimensions should not be considered limiting on the current disclosure. In various embodiments, $W_B' \geq W_{P1}'$ and $W_B' \geq W_{P2}'$; however, in various other embodiments, $W_B' < W_{P1}'$ or $W_B' < W_{P2}'$.

As shown in FIG. 6, in various embodiments, the calibration masses 106" may define a calibration mass thickness $W_S'$. In the current embodiment, $W_S' > W_{P1}' + W_{P2}' + W_B'$. In other embodiments, $W_S' > W_{P1}' + W_B'$ or $W_S' > W_{P2}' + W_B'$. In addition, in various embodiments, the upper surface 108" of the calibration masses 106" may extend above the upper surface 104" of the first piezoelectric crystal 102". Additionally, the lower surface 404" of the calibration masses 106" may extend below the lower surface 304" of the second piezoelectric crystals 302". However, in various other embodiments, the upper surface 108" may not extend above the upper surface 104" or the lower surface 404" may not extend below the lower surface 304". Additionally, in various other embodiments, the size, shape, and length of the calibration masses 106" may be used to regulate stiffness of the sensor 100" without changing the total mass of the sensor 100". In the current embodiment, the calibration masses 106 have a rectangular cross-section as shown in FIG. 6. However, in other various embodiments, the shape and cross-section of the calibration masses may be different shape such as a triangular or circular cross-section or a cylindrical or rectangular cuboid shape.

Additionally, as shown in FIG. 6, in various embodiments, the vibration sensor 100" may not include a washer and first contact between the bolt 118" and the first piezoelectric crystal 102". In these embodiments, the bolt 118" may be in direct contact with the first piezoelectric crystal 102". Additionally, in various embodiments, the vibration sensor 100" may not include a washer and nut between the spacer 204" and second piezoelectric crystal 302". In these embodiments, the spacer 204" may be in direct contact with the second piezoelectric crystal 302". Furthermore, in various embodiments, the sensor 100" may not include a nut between the spacer 204" and a pipe 612. In these embodiments, the spacer 204" may be in direct contact with the pipe 612. In various other embodiments, a nut may separate the spacer 204" from a pipe 612.

As shown in FIG. 6, in some embodiments, the vibration sensor 100" may include a first wire 124" and a second wire 126". In these embodiments, the first wire 124" may be directly connected to the first piezoelectric crystal 102" and the second wire 126" may be connected to the second piezoelectric crystal 302". However, in various other embodiments, the wires may be connected to the vibration sensor 100" at other positions on the vibration sensor 100" as described above.

FIG. 7 is a top view of a base of the vibration sensor 100" shown in FIG. 6. As shown in FIG. 7, in various embodiments, the base 400" may be a disc and may be made of brass; however, various materials and shapes may be present in various other embodiments. As shown in FIG. 7, in various embodiments, the base 400" includes an attachment section 402" and N calibration masses 106" exterior to the attachment section 402". In the current embodiment, N=8 and the base has eight calibration masses 106a"-h". Additionally, in various embodiments, the calibration masses 106" may be spaced equally around the base 400" such that the angles between calibration masses 106" may be 120°, 90°, 72°, 60°, 45°, or any other angle. Furthermore, in various embodiments, the calibration masses 106" may be spaced asymmetrically or at varying angles around the base 400". In addition, as is shown in FIG. 7, in various embodiments, the attachment section 402" of the base 400" may include an upper attachment surface 416", a lower surface, and a fastener hole 700. When the vibration sensor 100" is assembled, a bolt 118" or other fastening mechanism may be inserted through the fastener hole 700.

Figure 8:
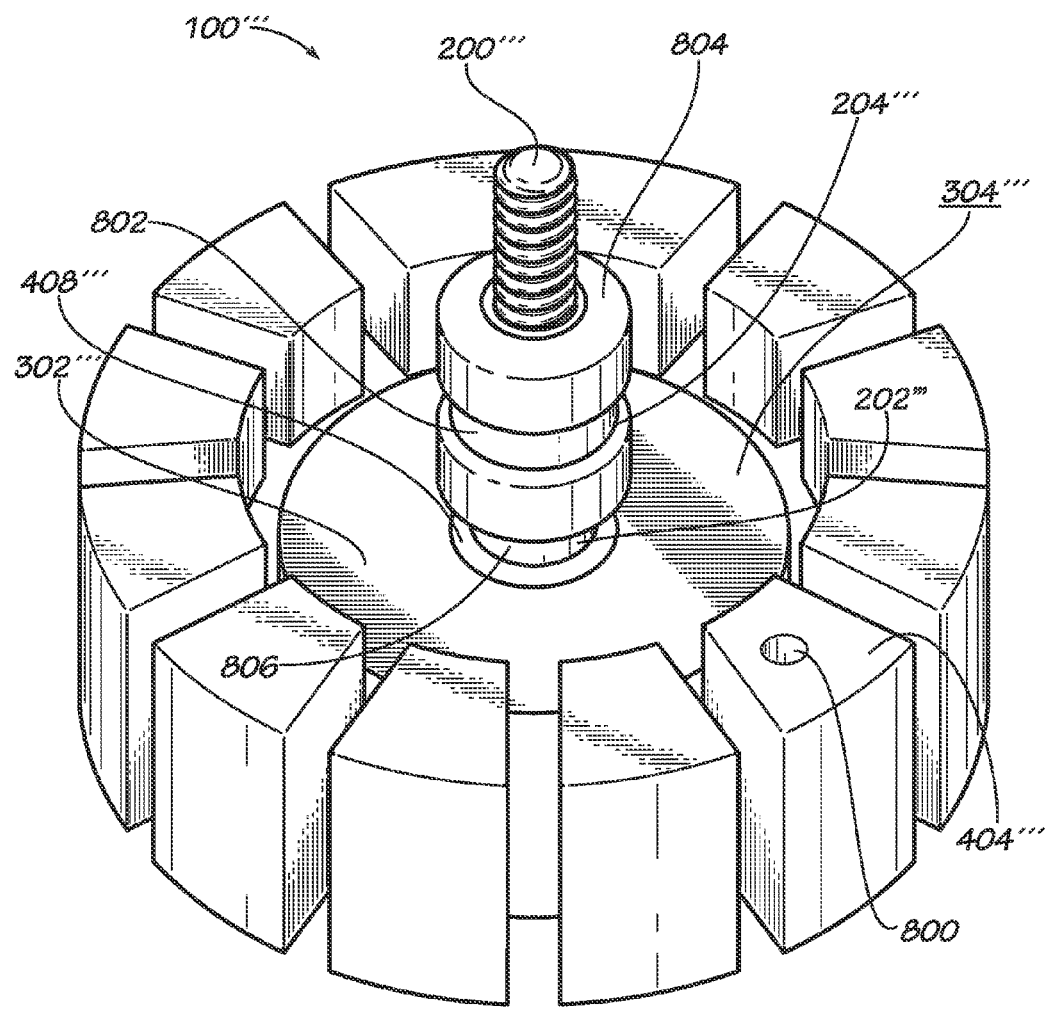
FIG. 8 is a perspective view of the vibration sensor shown in FIG. 1.

FIG. 8 is a perspective view of a vibration sensor 100'" in accordance with another embodiment of the current disclosure. As shown in FIG. 8, in various embodiments, a calibration mass 404'" may define an attachment bore 800. In the current embodiments, the attachment bore 800 may be on a lower surface 404'" of a calibration mass 106'". In these embodiments, a second contact may be connected to the calibration mass 106'" with a machine screw through a fastener hole of the second contact and into the attachment bore 800. In various other embodiments, the attachment bore 800 may be defined on an upper surface of the calibration mass 106''' or any other desirable portion of the calibration mass 106'''.

Additionally, as shown in FIG. 8, in various embodiments, the vibration sensor 100''' may also include a nut 202''' and a spacer 204''' below the lower surface 304''' of the second piezoelectric crystal 302''' and washer 408'''. In various embodiments, the spacer 204''' may have a cylindrical shape; however, in various other embodiments, the spacer 204''' may have a different shape. Additionally, in various embodiments, the spacer 204''' may define a groove 802 between a first end 804 of the spacer 204''' and the second end 806 of the spacer 204'''. In various embodiments, the nut 202''' may define a bore or bores similar to first bore 500 or second bore 502 for mating with a bolt 118 and an attachment screw 200''', respectively, or other attachment mechanism. As shown in FIG. 8, when vibration sensor 100''' is assembled, the attachment screw 200''' may be threaded through at least a portion of the spacer 204''' of the nut 202'''.

Although two piezoelectric crystals 102,302, and a base 400 are shown in the present embodiments, in various embodiments any number of piezoelectric crystals or bases may be used. For example, in various embodiments, the vibration sensor 100 may only include a first piezoelectric crystal 102 and a base 400. In various other embodiments, more than two piezoelectric crystals 102,302 or more than a single base 400 may be present. In various other embodiments with more than two piezoelectric crystals 102,302 and more than one base 400, a series of piezoelectric crystal and base combinations may be in a stacked arrangement aligned on one bolt 118. In this arrangement, the crystal/base combinations may be connected together using an adhesive. In various other embodiments, the adhesive may be double-sided tape, various glues, various coatings including elastomeric and silicon coatings among others, pure adhesives, or by a fastener such as bolt 118. In various other embodiments, an adhesive may not be included. In such embodiments, a non-conducting spacer may be used, such as a nylon or rubber spacer. In other embodiments, conduction may not be a concern if each base is connected to the same ground. This stacked arrangement may have a different response from other orientations.

Figure 9:
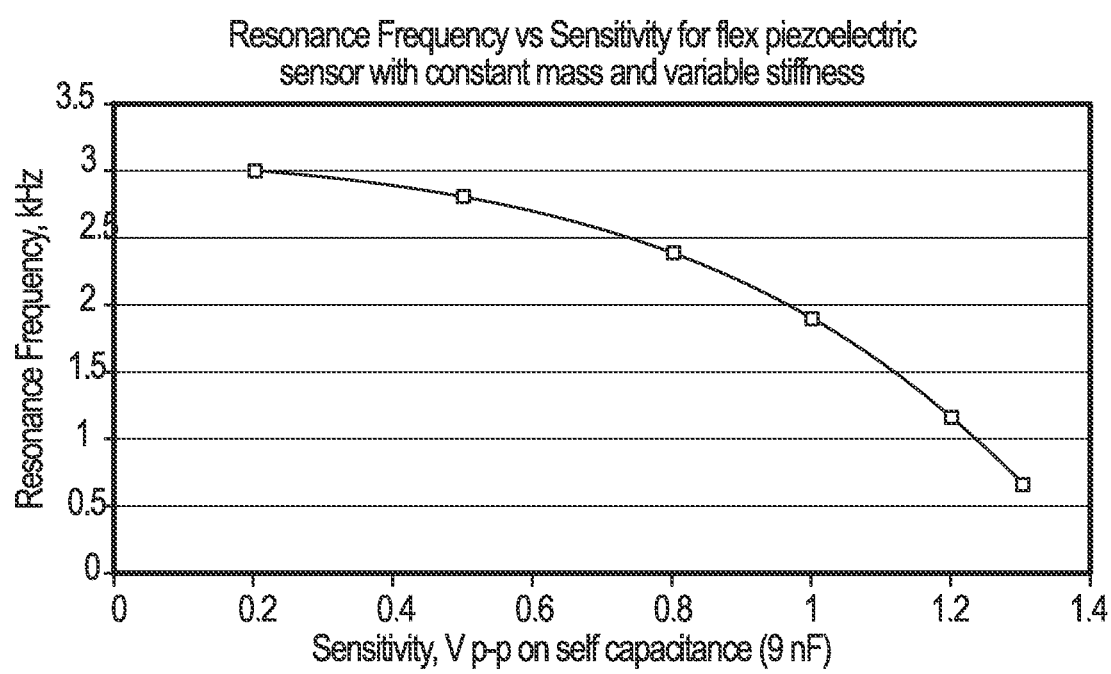
FIG. 9 is a chart showing the relationship between resonance frequency and sensitivity for a vibration sensor.

As shown in FIG. 9, in various embodiments the sensitivity of the vibration sensor 100 may be altered by changing a stiffness of the vibration sensor while changing the total mass of the sensor 100 to a less degree. The resonance of an item may be defined as the tendency to oscillate or to vibrate with greater amplitude at some frequencies over others. The resonance frequency of an item may be defined as the frequency at which the response amplitude is at a relative maximum. The sensitivity of an item may be defined as the minimum magnitude of an input signal required to produce a specified output signal. Piezoelectric sensor resonance frequency and sensitivity may be defined by the following equations:

$$\text{Resonance Frequency} = K * \left(\frac{\text{Stiffness}}{\text{Mass}}\right)^{\frac{1}{2}}$$

$$\text{Sensitivity} = N * \left(\frac{\text{Mass}}{\text{Stiffness}}\right)$$

where the coefficients K and N are based on the sensitivity of the ceramic material of the piezoelectric crystal and, to a lesser extent, on the construction of the sensor. More specifically, coefficient K is slightly less than $\frac{1}{2}\pi$, depending on the system damper properties. More specifically, $K \approx 0.15$ in the current embodiment. Coefficient N directly depends on the sensitivity of the piezoelectric (piezo-module) and the sensor construction. In particular, the piezo-module may be defined as a ratio of the charge and force which created that charge at the piezoelectric.

As indicated by the above formulas, the sensitivity of the sensor 100 is proportional to its total mass and inversely proportional to its stiffness. The resonance frequency is proportional to the sensor 100's stiffness and inversely proportional to its total mass. In traditional compression and shear mode piezoelectric sensors, it is not typical to alter the stiffness of construction of the sensors; instead, only total mass and the sensitivity of the ceramic material may be altered to provide a suitable sensor. However, these sensors have limited use for many fluid leak applications because they are typically not flexible enough to achieve a fixed resonance frequency required by fluid leak applications since only total mass is typically altered.

In various embodiments, the vibration sensor 100 with the calibration masses 106 allows the parameter of stiffness of the vibration sensor 100 to be greatly adjusted. Even though the calibration masses 106 add mass to the vibration sensor 100, the position of the calibration masses 106 exterior to the attachment section 402 greatly increases the flexibility of the base 400, thereby lowering the stiffness of the vibration sensor 100 to a much greater degree. The ability to adjust the stiffness parameter may provide more flexibility to get a required sensitivity. In particular, in various embodiments, the stiffness of the sensor may be altered by changing the size, shape, or length of the calibration mass 106. The use of calibration masses 106 to change the stiffness of the sensor 100 allows for finding an optimal ratio of sensitivity and resonance frequency for a particular sensor application. In various embodiments, the vibration sensor 100 may achieve a high sensitivity with a resonance frequency around 3000 Hz. In various embodiments, the optimal ratio of sensitivity and frequency range is at a sensitivity of about 0.6 V p-p and at a resonance frequency of 2700 Hz, though other optimal ratios may be present in various embodiments and the disclosure of an optimal ratio on the current embodiment should not be considered limiting on the current disclosure. In various embodiments, the vibration sensor 100 may have a resonance frequency which is tuned to an anticipated frequency of vibrations generated by an anticipated leak in a piping member. The resonance frequency may be tuned in some embodiments and may not be tuned in others.

A method of manufacturing and assembly of a vibration sensor 100 is also disclosed. In various embodiments, the base 400 of the vibration sensor 100 may be formed with the attachment section 402 and the calibration mass 106 exterior to the attachment section 402. As discussed previously, in various embodiments, the calibration mass thickness $W_S$ is greater than the attachment section 402 thickness $W_B$.

In various embodiments, after the base 400 has been formed, the first piezoelectric crystal 102 and the second piezoelectric crystal 302 may be positioned on the base 400. In various embodiments, the piezoelectric crystals 102,302 may be positioned such that the lower surface 412 of the first piezoelectric crystal 102 may be adjacent to the upper attachment surface 416 of the attachment section 402. The upper surface 414 of the second piezoelectric crystal 302 may be adjacent to the lower attachment surface 418 of the attachment section 402. In various embodiments, the first piezoelectric crystal 102 and second piezoelectric crystal 302 may be attached to the base 400 with an adhesive that allows a current to pass through. In various embodiments, the adhesive allows for conductivity and flexibility. In various embodiments, a silver conductive epoxy adhesive is the adhesive. In the current embodiment, the 8330S Silver Conductive Epoxy Adhesive: Slow Cure/Extreme Conductivity epoxy sold by MG Chemicals® may be used as an adhesive. In other embodiments, the piezoelectric crystals 102,302 may be bonded or attached to the base 400 through other suitable means such as double-sided tape, various glues, various coatings including elastomeric and silicon coatings among others, pure adhesives, or by a fastener such as bolt 118.

In various embodiments, the first washer 112 may be disposed on the first piezoelectric crystal 102 such that a polishing surface similar to polishing surface 420a is in contact with the upper surface 104 of the first piezoelectric crystal 102. A first contact 110 may then be positioned above the first washer 112 such that the polishing surface similar to polishing surface 420b is in contact with the first contact 110. The second washer 408 may be disposed on the second piezoelectric crystal 302 such that a the polishing surface similar to polishing surface 422a,b is in contact with the lower surface 304 of the second piezoelectric crystal 302.

In various embodiments, the nut 202 may be included and may be positioned such that the nut 202 is between the securing bore 500 of the spacer portion 204 and the washer 408. To secure the vibration sensor 100 to the spacer portion 204, the bolt 118 may be provided in various embodiments. In particular, in the current embodiment, to secure the vibration sensor 100, the bolt 118 is threaded through the fastener hole of the first contact 110, washer 112, a fastener hole 428 of the first piezoelectric crystal 102, a fastener hole of the base similar to fastener hole 700 of the base 400", a fastener hole 430 of the second piezoelectric crystal 302, washer 408, and nut 202 and into the securing bore 500 of the spacer portion 204. In the current embodiment, the spacer portion 204 may then accept an attachment screw 200 into the securing bore 502 to secure the vibration sensor 100 to a pipe similar to pipe 612.

As shown in FIG. 1, in various embodiments, a second contact 114 may be disposed on an upper surface 108 of the calibration mass 106 of the base 400. The second contact 114 may be connected to the calibration mass 106 with a contact screw 116 through the fastener hole of the second contact 114 and into an attachment bore defined in the upper surface 108. In various embodiments, the vibration sensor 100 may further include electrical connections, such as wires 124, 126, connecting the vibration sensor 100 with a connection terminal 130. In various embodiments, wires 124,126 may be soldered to the first contact 110 and second contact 114, respectively, or soldered directly to the first piezoelectric crystal 102, second piezoelectric crystal 302, or base 400. The wires 124,126 may then connect to terminal 130 in a connector housing 128. This connection may allow for connection to a processing device or another electrical device so that the charge differential may be handled electronically, which may include recordation, amplification, summation, digital processing, and a number of other electrical features.

A method of detecting a vibration with the vibration sensor 100 is also disclosed. In various embodiments, the vibration sensor 100 may be mounted to a water distribution system. In various embodiments, the vibration sensor 100 may be mounted to a pipe similar to the pipe 612 in the water distribution system. In the current embodiment, the vibration sensor 100 may be mounted to the outside of a pipe 612 in the water distribution system. In other embodiments, the vibration sensor 100 may be mounted to other parts of the water distribution system including a valve, pipe coupling, fitting, or any other location suitable for vibration detection. In various embodiments, the vibration sensor 100 may be mounted on the water distribution system with a screw 200. In yet other embodiments, the vibration sensor 100 may be mounted on the water distribution system with a magnet or series of magnets. However, in various other embodiments, any suitable mounting mechanism may be utilized to mount the vibration sensor 100 to the water distribution system, such as to a pipe similar to the pipe 612.

In the current embodiment, after the vibration sensor 100 is mounted to the pipe 612, the vibration sensor 100 detects mechanical vibration in the pipe in a frequency range associated with a water leak. The piping system may translate vibrations produced by leaks throughout piping members in the system. Moreover, the ground may conduct some vibrations as well. The vibrations may be translated through the piping system, particularly through the rigid materials making up the system, including cast iron or steel piping in various embodiments. This translated vibration may travel through the piping system to the bolt 118 and into the vibration sensor 100. In various other embodiments, the translated vibration may travel through the piping system to the magnet. In various embodiments, the vibration sensor 100 may detect mechanical vibrations in the range of 100-1500 Hz. In various other embodiments, the vibration sensor may detect mechanical vibrations above 1500 Hz or below 100 Hz. Although the mechanical translation of vibrations described above provides sufficient vibration for detection of leaks in the current embodiment, in various other embodiments the piping system may also translate acoustic vibration which may be sufficient of itself to allow detection by the vibration sensor 100 as well.

In various embodiments, after the vibration is translated into the vibration sensor 100, the piezoelectric crystals 102,302 may generate an electric current. In various embodiments, the current may be transmitted via leads to a terminal 130 that may later be connected to a circuit board similar to circuit board 600 where the current is processed for the detection of a leak. The detection of a leak may then be communicated to a processor that includes a leak detection algorithm. In various embodiments, the processor may convert the amplitude of the vibration into a voltage proportional to the vibration. In various other embodiments, the processor may convert the amplitude of the vibration into a current proportional to the vibration. In yet other various embodiments, the processor may convert the amplitude of the vibration into both a voltage proportional to the vibration and a current proportional to the vibration. After the vibration amplitude is converted to a voltage or current or both, an external logic solver may compare the vibration signal level to a predetermined threshold level. The predetermined threshold level may be used to determine whether a detected vibration is at an acceptable level. For example, in various embodiments, a vibration below the predetermined threshold level may be an acceptable vibration. If the converted amplitude of vibration surpasses or exceeds the predetermined threshold level, the event is marked as an trigger event. In various embodiments, the trigger event may cause an alert signal to be sent to a utility provider for further analysis. In other various embodiments, the trigger event may set off an alarm at the utility provider warning of a vibration above the acceptable predetermined threshold level. In practice, this vibration sensor will detect water leaks and allow conservation of water and funds normally lost in water leaks.

One should note that conditional language, such as, among others, "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more particular embodiments or that one or more particular embodiments necessarily include logic for deciding, with or without user input or prompting, whether these features, elements, or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A sensor comprising:
    at least one piezoelectric crystal having an upper surface and a lower surface;
    a base having an attachment section defining an attachment surface, a first calibration mass, a second calibration mass, and a notch between the first calibration mass and the second calibration mass, the first calibration mass comprising a first calibration mass thickness greater than a thickness of the attachment section of the base, and the second calibration mass comprising a second calibration mass thickness greater than the thickness of the attachment section of the base, the base further defining an axis therethrough;
    wherein a one of the at least one piezoelectric crystal upper surface and lower surface attaches to the attachment surface of the base; and
    wherein the at least one piezoelectric crystal is positioned radially inward from the first calibration mass and the second calibration mass relative to the axis of the base.

2. The sensor of claim 1, wherein the first calibration mass and the second calibration mass each define a radially innermost edge defining a radius, and the at least one piezoelectric crystal defines a radially outermost edge defining a radius, and wherein the radius of the radially outermost at least one piezoelectric crystal is less than the radius of the radially innermost edge of the first calibration mass and the second calibration mass.

3. The sensor of claim 1, wherein the first calibration mass and the second calibration mass define an outer rim of the base.

4. The sensor of claim 1, wherein the second calibration mass thickness is equal to the first calibration mass thickness.

5. The sensor of claim 1, wherein the base includes at least three calibration masses, each of the at least three calibration masses having a calibration mass thickness greater than a combined thickness of the at least one piezoelectric crystal and the attachment section.

6. The sensor of claim 1, wherein the first calibration mass is wedge-shaped and defines a rectangular cross-section.

7. The sensor of claim 1, wherein the lower surface of the piezoelectric crystal is attached to the attachment surface of the base, and wherein the first calibration mass extends above the upper surface of the at least one piezoelectric crystal.

8. The sensor of claim 1, wherein the first calibration mass thickness is greater than a combined thickness of the attachment section of the base and the at least one piezoelectric crystal.

9. The sensor of claim 1, wherein the at least one piezoelectric crystal is a first piezoelectric crystal, the vibration sensor further comprising a second piezoelectric crystal having an upper surface and lower surface, the upper surface of the second piezoelectric crystal attached to a second attachment surface of the attachment section of the base.

10. The sensor of claim 9, wherein the first calibration mass thickness is greater than a combined thickness of the attachment section, the first piezoelectric crystal, and the second piezoelectric crystal.

11. A method of manufacturing a sensor comprising:
    forming a base of the vibration sensor with an attachment section defining an attachment surface, a first calibration mass, a second calibration mass, and a notch between the first calibration mass and the second calibration mass, the first calibration mass comprising a first calibration mass thickness greater than a thickness of the attachment section of the base, and the second calibration mass comprising a second calibration mass thickness greater than the thickness of the attachment section of the base, the base further defining an axis therethrough; and
    attaching a piezoelectric crystal to the attachment surface of the attachment section of the base, the piezoelectric crystal positioned radially inward from the first calibration mass and the second calibration mass relative to the axis of the base.

12. The sensor of claim 11, wherein the first calibration mass and the second calibration mass each define a radially innermost edge defining a radius, and the piezoelectric crystal defines a radially outermost edge defining a radius, and wherein the radius of the radially outermost at least one piezoelectric crystal is less than the radius of the radially innermost edge of the first calibration mass and the second calibration mass.

13. The method of claim 11, further comprising attaching a second piezoelectric crystal to a second attachment surface of the attachment section of the base.

14. The method of claim 11, wherein the first calibration mass thickness is greater than a combined thickness of the piezoelectric crystal and the attachment section of the base.

15. A method of detecting vibrations with a sensor comprising:
- attaching the sensor to a piping member, the sensor including:
  - at least one piezoelectric crystal having an upper surface and a lower surface; and
  - a base having an attachment section defining a first calibration mass, a second calibration mass, and a notch between the first calibration mass and the second calibration mass, the first calibration mass comprising a first calibration mass thickness greater than a thickness of the attachment section of the base, and the second calibration mass comprising a second calibration mass thickness greater than the thickness of the attachment section of the base, the base further defining an axis therethrough;
  - wherein the attachment section defines an attachment surface;
  - wherein a one of the upper surface and the lower surface of the at least one piezoelectric crystal attaches to the attachment surface of the attachment section; and
  - the at least one piezoelectric crystal positioned radially inward from the first calibration mass and the second calibration mass relative to the axis of the base;
- monitoring a signal output of the sensor;
- receiving a signal output from the sensor; and
- determining that the signal indicates that a vibration has been sensed.

16. The sensor of claim 15, wherein the first calibration mass and the second calibration mass each define a radially innermost edge defining a radius, and the at least one piezoelectric crystal defines a radially-outermost edge defining a radius, and wherein the radius of the radially outermost at least one piezoelectric crystal is less than the radius of the radially innermost edge of the first calibration mass and the second calibration mass.

17. The method of claim 15, wherein receiving the signal output includes converting a vibration signal amplitude into a proportional signal for processing in a processor.

18. The method of claim 15, wherein determining that a signal indicates that a vibration has been sensed includes comparing the received signal output with a predetermined threshold level.

19. The method of claim 18, wherein the received signal output is marked as a trigger event if the received signal output surpasses the predetermined threshold level.

20. The method of claim 19, further comprising sending an alert signal to a utility provider when a trigger event is determined.

* * * * *